United States Patent
Goldmann et al.

(10) Patent No.: US 8,075,612 B2
(45) Date of Patent: Dec. 13, 2011

(54) TEXTILE VASCULAR PROSTHESIS WITH A COATING

(75) Inventors: Helmut Goldmann, Tuttlingen (DE); Christof Merckle, Mannheim (DE); Shalaby W. Shalaby, Anderson, SC (US)

(73) Assignees: Aesculap AG (DE); Poly-Med, Inc., Anderson, SC (US)

( * ) Notice: Subject to any disclaimer, the term of this patent is extended or adjusted under 35 U.S.C. 154(b) by 430 days.

(21) Appl. No.: 12/513,696

(22) PCT Filed: Nov. 7, 2007

(86) PCT No.: PCT/EP2007/009635
§ 371 (c)(1),
(2), (4) Date: May 13, 2009

(87) PCT Pub. No.: WO2008/058660
PCT Pub. Date: May 22, 2008

(65) Prior Publication Data
US 2009/0234442 A1    Sep. 17, 2009

(30) Foreign Application Priority Data
Nov. 13, 2006    (DE) .................... 10 2006 053 752

(51) Int. Cl.
*A61F 2/06* (2006.01)
(52) U.S. Cl. ...................................... 623/1.46; 442/123
(58) Field of Classification Search .................. 623/1.46
See application file for complete search history.

(56) References Cited

U.S. PATENT DOCUMENTS

| 6,462,169 | B1 | 10/2002 | Shalaby |
| 6,706,058 | B2 | 3/2004 | Hierlemann et al. |
| 2004/0109892 | A1 | 6/2004 | Shalaby |

FOREIGN PATENT DOCUMENTS

| DE | 102 54 215 A1 | 6/2004 |
| EP | 0 628 587 A2 | 12/1994 |
| EP | 0 693 294 A2 | 1/1996 |
| EP | 0 908 482 A1 | 4/1999 |
| EP | 1 112 724 A2 | 7/2001 |
| EP | 1 430 914 A1 | 6/2004 |
| EP | 1 181 541 B1 | 3/2005 |
| EP | 1 181 941 B1 | 4/2006 |
| WO | 03/037957 A1 | 5/2003 |
| WO | 2004/045663 A1 | 6/2004 |
| WO | 2006/055049 A1 | 5/2006 |

OTHER PUBLICATIONS

Zhaoxu Wang et al., "Evaluation of biodegradable synthetic scaffold coated on arterial prostheses implanted in rat subcutaneous tissue," Biomaterials 26, Dec. 1, 2005, pp. 7387-7401.

*Primary Examiner* — Lynda Salvatore
(74) *Attorney, Agent, or Firm* — DLA Piper LLP (US)

(57) ABSTRACT

Textile vascular prostheses having a coating include an absorbable polymer in the form of a three-armed polyester having terminal hydroxyl groups from hydroxy acids polymerized onto a central trifunctional hydroxy compound, the three arms being tetrapolymers of lactide, ε-caprolactone, trimethylene carbonate and glycolide. The polymer is composed of about 30 to about 45 mol % of lactide, about 20 to about 40 mol % of ε-caprolactone, about 10 to about 28 mol % of trimethylene carbonate and about 10 to about 25 mol % of glycolide.

14 Claims, No Drawings

TEXTILE VASCULAR PROSTHESIS WITH A COATING

RELATED APPLICATIONS

This is a §371 of International Application No. PCT/EP2007/009635, with an international filing date of Nov. 7, 2007 (WO 2008/058660 A2, published May 22, 2008), which is based on German Patent Application No. 102006053752.1, filed Nov. 13, 2006.

TECHNICAL FIELD

This disclosure relates to a textile vascular prosthesis having a coating composed of an absorbable polymer in the form of a three-armed polyester having terminal hydroxyl groups from organic hydroxy acids polymerized onto a central trifunctional hydroxy compound, the three arms being tetrapolymers of lactide, $\epsilon$-caprolactone, trimethylene carbonate and glycolide.

BACKGROUND

Polymers of the kind mentioned and their use for coating vascular prostheses are described in US 2004/0109892 A1, the contents of which are hereby incorporated herein. Those polyesters are useful for many applications. In the case of coating polymers for textile vascular prostheses, however, in vivo tests have shown that unexpected problems can arise. One coating polymer, similar in composition to that described in Example 1, was found to become detached from the walls of a prosthesis after implantation, and to be ascertainable for a very prolonged period in adjacent connective tissue, where it caused inflammatory reactions.

It could therefore be helpful to provide a coated textile vascular prosthesis that exhibits good ingrowth behavior in the body and does not give rise to detachment problems and inflammatory side-reactions.

SUMMARY

We provide a textile vascular prosthesis having a coating comprising an absorbable polymer in the form of a three-armed polyester having terminal hydroxyl groups from hydroxyl acids polymerized onto a central trifunctional hydroxyl compound, the three arms being tetra-polymers of lactide, $\epsilon$-caprolactone, trimethylene carbonate and glycolide, wherein the polymer is composed of about 30 to about 45 mol % of lactide, about 20 to about 40 mol % of $\epsilon$-caprolactone, about 10 to about 28 mol % of trimethylene carbonate and about 10 to about 25 mol % of glycolide.

DETAILED DESCRIPTION

We provide a vascular prosthesis wherein the polymer is composed of about 30 to about 45 mol % of lactide, about 20 to about 40 mol % of $\epsilon$-caprolactone, about 10 to about 28 mol % of trimethylene carbonate and about 10 to about 25 mol % of glycolide.

Intensive tests have shown that a coating polymer, or an impregnation, having the composition described herein meets coating requirements. The polymer has good adherence properties to the textile prosthesis so that there is no risk of detachment. The coating polymer is sufficiently flexible to comply with movements of the prosthesis. The coating polymer, despite its molecular size and its sterical construction, is sufficiently soluble in environmentally compatible coating solvents, and is sufficiently rapidly degraded in vivo after implantation, so that it is replaced by the ingrowing connective tissue.

The trifunctional hydroxy compound preferably has a central nitrogen atom in a manner known per se. Triethanolamine is particularly useful as trihydroxy compound. The polymer may be a segmented polymer comprising three first segments (segment I) connected by the trifunctional hydroxy compound and three second segments (segment II) connected to the free ends of the first segments, the first segments differing from the second segments.

It will be found advantageous for the first segment to be free of lactide. Preferably, the first segment is formed from caprolactone, trimethylene carbonate and glycolide.

The second segment is preferably free of trimethylene carbonate. Advantageously, the second segment is formed from lactide, glycolide and optionally caprolactone. In particularly preferred polymers, the second segment is free of caprolactone, being formed of lactide and glycolide only.

The hydroxy acids are used in a conventional manner in the form of cyclic monomers which polymerize via ring opening. The properties of the copolymers, more precisely terpolymers, can be influenced within the already relatively narrow limits of the molar ratios of the monomers. Thus, preferred polymers contain about 30 to about 40 mol % of lactide, particularly about 30 to about 35 mol %. The percentage share of $\epsilon$-caprolactone is preferably in the range from about 24 to about 40 mol %, particularly from about 31 to about 40 mol %. The molar fraction of trimethylene carbonate is preferably in the range from about 10 to about 20 mol %, particularly about 12 to about 16 mol %. The percentage molar fraction of glycolide is preferably in the range from about 15 to about 20 mol %, particularly about 16 to about 19 mol %. The polymers are, in particular, free of other monomers.

Further advantageous specifications are also possible within the segments. Preferably, the first segment contains about 30 to about 40 mol %, particularly about 32 to about 35 mol % of caprolactone, based on the total amount of the monomers in the two segments. The molar fraction of trimethylene carbonate in the first segment is preferably about 10 to about 20 mol %, particularly about 13 to about 17 mol %. The fraction of glycolide in the first segment is preferably in the range from about 7 to about 12 mol %, particularly about 8 to about 11 mol %, again based on the total amount of the monomers in the two segments.

It is similarly possible to also specify the molar composition of the second segment. Preferably, the lactide fraction in the second segment is in the range from about 30 to about 45 mol %, particularly about 32 to about 42 mol %. The lactide fraction is preferably present in the form of L-lactide. DL-Lactide can also be used.

The ratio of lactide to glycolide in the second segment is generally about 20:1 to 4:1, and a range from 5:1 to 4:1 is preferred.

Caprolactone is preferably present in the second segment in amounts from about 0 to about 4 mol %. The fraction of glycolide in the second segment is preferably about 1 to about 10 mol %, particularly about 2 to about 8 mol %.

Owing to the high lactide fraction in the second segment, the latter has a substantially crystalline character and therefore is also referred to as a hard segment. By comparison, the first segment is substantially amorphous and can also be referred to as a soft segment. Variations in the properties of the coating are also possible by having different polymers of the recited kind present together in the coating in admixture with each other.

The molecular weight ($M_w$) of the polymers in the coating is generally in the range from about 100 to about 180, particularly in the range from about 130 to about 150 kilodaltons. The number average molecular weight ($M_n$) is generally in the range from about 65 to about 100 and preferably in the range from about 70 to about 85 kilodaltons, particularly about 72 to about 82 kilodaltons. The $M_w/M_n$ ratio is generally in the range from about 1.0 to about 3.3, preferably in the range from about 1.5 to about 2.1, particularly about 1.6 to about 2.1.

The polymers for the coating are obtainable in a conventional manner, as described in US 2004/0109892 A1 and U.S. Pat. No. 6,462,169, the subject matter of which is hereby incorporated herein by reference.

Coating solutions of the polymers can be prepared by dissolving the polymers in suitable solvents, in which case solvents in which the polymers gel as the solution cools are preferred. The gelled polymeric state is particularly advantageous for performing the coating and for achieving dense coatings. Preferred solvents are ketones, particularly 3-pentanone. Halogenated hydrocarbons are not required, which goes for fluorinated hydrocarbons in particular, and this is advantageous for the residual solvent content of the prosthesis.

The coating polymers may contain bioactive components, if desired. Examples of contemplated bioactive components include growth factors and antibiotically active substances, particularly metallic silver or silver salts in a very fine state of subdivision, or antithrombo-genically acting agents. Additions of this kind are known.

Chemical modification of the polymers themselves, particularly crosslinking of the polymers in the coating, is not required and also not desired. As a result, the polymers can be degraded through simple hydrolysis.

The textile vascular prosthesis is preferably a knitted or woven prosthesis in which the pore size, or the permeability of the prosthesis walls, can be adjusted through the manner of knitting and weaving and the kind of threads used. The prosthesis may typically include pleating. Furthermore, the prosthesis may have at least one bifurcation or be equipped with branch points. The vascular prosthesis may also comprise a vascular patch, i.e., a sheetlike piece of walling, which is useful for example to replace a defect vascular wall or for closing an opening in a vascular wall. The prosthesis may also be provided with an external spiral which is coated together with the prosthesis.

The material from which the prosthesis is fabricated is generally polyethylene terephthalate. The threads used are normally multifil. They can be constructed as flat threads and/or as velour threads. The diameter of the vascular prostheses can be between about 4 and about 40 mm. The large diameters are contemplated for vascular prostheses near the heart. The vascular prosthesis may also have a curvature which corresponds to the aortic arch.

Further features of our protheses will be apparent from the following description of representative examples. The individual features can each be actualized in any variation by themselves or in combinations of two or more thereof.

General Preparative Example of Synthesis of Crystalline, Segmented Triaxial Copolyesters The first step is to prepare amorphous, monocentric, triaxial polymeric initiators as intermediates (from trifunctional hydroxy compound and the monomers of segment I). These are subsequently end grafted with selected mixtures of the cyclic monomers of segment II to form crystalline terminal segments II.

To prepare the polymeric initiator/intermediate (segment I), the monomers caprolactone, trimethylene carbonate and glycolide are each added in the form of cyclic monomers together with predried triethanolamine and tin(II) 2-ethylhexanoate to a stainless steel reactor equipped for mechanical stirring and vacuum use. The contents are dried for one hour at 40° C. under vacuum and brought to a pressure equilibrium with dry nitrogen. The contents are stirred to ensure complete mixing and the temperature is raised to 180° C. The reaction is continued at 180° C. until at least a 50% and preferably 100% monomer conversion is achieved (as determined by high pressure liquid chromatography—HPLC or by gas chromatography—GC). The polymeric initiator is then either cooled down and maintained at room temperature for about 15 hours, or maintained at a temperature of 180° C. until the next step.

The polymeric initiator is then, as appropriate, heated/cooled to 110° C. and the monomeric components of segment II (lactide, optionally caprolactone and glycolide) are added in their respective amounts. The mixture is stirred until the polymeric initiator has dissolved. Then, the temperature is raised to 160° C. In the case of polymers having a total monomer/catalyst molar ratio of 28 000, a further identical amount of tin(II) 2-ethylhexanoate is added before the temperature is raised to 160° C. The contents are stirred for a further 30 minutes or so after the temperature has reached 160° C. Stirring is then stopped and the reaction to form segment II is continued by heating to 130-150° C. until virtually complete conversion is achieved (deter-mined by HPLC or GC).

After the polymerization has ended, the polymer is discharged and comminuted into pieces about 2.5 cm in size. Residual monomers are stripped off by distillation under reduced pressure at temperatures up to 80° C. The polymer is then further purified by precipitation from a solution of 20% (weight/volume) in dichloromethane (DCM) by using 2 parts by volume of isopropyl alcohol (IPA) at −60° C. in a commercially available mixer. The purified polymer is then dried at not more than 80° C. under reduced pressure to constant weight. Further purification is effected by precipitating the purified polymer from a concentrated acetone solution by pouring into 2-propanol. A dry product is isolated therefrom.

Coating of Vascular Prosthesis

A vascular prosthesis with pleating is pulled over a rod and fixed in the elongate position, substantially eliminating the pleating.

A suitable amount of the coating polymer is dissolved in 3-pentanone at about 80° C. to form an approximately 10% (weight/volume) solution. The solution is allowed to cool down, and the polymer assumes a gel state. The rod with the expanded vascular prosthesis is repeatedly dipped into this gel. Excess gel is allowed to drip off the prosthesis between the dips, and the prosthesis is moved at the same time to obtain a uniform coating. Between the particular dips, the prosthesis is dried at room temperature for 2 hours in each case. Thereafter, the coating on the vascular prosthesis is dried and fixed at 60° C.

There are numerous possible variations for performing the coating. The coating solution can also be brushed or sprayed on. The coating solution can also be drummed in. Furthermore, the prosthesis can be turned inside out prior to coating or between individual coating operations, so that the inner wall of the prosthesis becomes the outer wall.

In this way, the prosthesis can be coated/impregnated on its outer wall, on its inner wall, inside and outside and also in the interior of the wall, depending on which method of coating is preferred.

In the dry state, the prosthesis wall is well-sealed by the film-forming coating. The coating adheres well to the prosthesis and is able to comply with movements of the prosthesis without fracture. No plasticizers of any kind are required.

Our protheses will now be more particularly elucidated by the examples which follow and the related description.

Examples 1 to 8

Polymer Composition

Tables 1-3 contrast the polymer compositions and also the physical data of the polymers according to Examples 1 to 8 with a polymer similar to Example 1 of US 2004/0109892 A1 (comparative example):

TABLE 1

| | Polymer composition | | | |
|---|---|---|---|---|
| Polymer charge | Composition [mol %] | | | |
| Comparative Example | L-Lactide | ε-CL | TMC | Glycolide |
| Similar to prior art | 40 | 30 | 26 | 4 |
| Example 1 | 36 | 24 | 26 | 14 |
| Example 2 | 36 (D,L-) | 24 | 26 | 14 |
| Example 3 | 36 | 34 | 16 | 14 |
| Example 4 | 42 | 32 | 16 | 10 |
| Example 5: mixture of 1 and 4 (50:50) | 39 | 28 | 21 | 12 |
| Example 6 | 34 | 35 | 14 | 17 |
| Example 7 | 32 | 35 | 14 | 19 |
| Example 8 | 33 | 35 | 14 | 18 |

The polymers differ in their overall composition, particularly with regard to the fractions of glycolide and lactide.

In the second series of polymers, the glycolide fraction was raised from 4% to a maximum of 19% and the L-lactide was lowered from 40 to 32%.

Table 2 lists the components of the two segments making up the random polymer:

TABLE 2

| | Polymer composition in segments 1 and 2 | |
|---|---|---|
| | Composition (mol %) | |
| Polymer charge | Segment 1 (soft) CL/TMC/G | Segment 2 (hard) LL/CL/G |
| Comparative Example | 26/26/4 | 40/4/0 |
| Example 1 | 22/26/8 | 36/2/6 |
| Example 2 | 22/26/8 | 36 (D,L-)/2/6 |
| Example 3 | 32/16/8 | 36/2/6 |
| Example 4 | 32/16/8 | 42/0/2 |
| Example 5 (50:50) | 27/21/8 | 39/1/4 |
| Example 6 | 35/14/9 | 34/0/8 |
| Example 7 | 35/14/11 | 32/0/8 |
| Example 8 | 35/14/10 | 33/0/8 |

The glycolide fraction was raised from 0 to 8% in segment 2 and from 4 to a maximum of 11% in segment 1. Examples 6 to 8 concern particularly preferred polymer compositions.

Table 3 recites the physical data of the coating polymers:

TABLE 3

| | Physical data | | | | | | |
|---|---|---|---|---|---|---|---|
| | Melting | | Heat of | Inherent | Molecular weight | | |
| Polymer charge | point [° C.] | $T_G$ [° C.] | fusion [J/g] | viscosity [dl/g] | $M_w$ [kDa] | $M_n$ [kDa] | $M_w/M_n$ |
| Comparative Example | 148 | −37 | 13.1 | 1.32 | 137 | 82 ± 9 | 1.66 |
| Example 1 | — | −3 | — | 1.16 | 132 | 72 | 1.83 |
| Example 2 | — | −4 | — | 1.23 | 137 | 73 | 1.88 |
| Example 3 | 121 | −28 | 7.9 | 1.45 | 144 | 82 | 1.76 |
| Example 4 | 149 | −37 | 15.8 | 1.49 | 142 | 81 | 1.75 |
| Example 5 (50:50) | 147 | −12 | 7.2 | 1.43 | 137 | 76 | 1.80 |
| Example 6 | 109 | −29 | 7.4 | 1.45 | 146 | 82 | 1.78 |
| Example 7 | 101 | −26 | 5.1 | 1.23 | 135 | 74 | 1.82 |
| Example 8 | 106 | −22 | 4.1 | 1.15 | 134 | 73 | 1.84 |

Inherent viscosity was measured at 25° C. in chloroform using 200 mg of sample/100 ml via capillary OC.

The polymer is dissolved at 80° C. in 3-pentanone to form a 10% solution and allowed to gel at 5° C. for 24 hours.

Coating is done on pleated 8 mm vascular prosthesis and an extended length of 22 cm on coating with prostheses pulled over a PE rod.

Coatings with freely suspended prostheses are carried out with pleated prostheses which were weighted with a 62 g weight and cut to a length of 25 cm.

The frames are in both cases repeatedly dipped into the coating solution in accordance with the information provided in the table.

The coating parameters follow from Table 4:

TABLE 4

| | Coating parameters | | | | |
|---|---|---|---|---|---|
| Polymer | Temperature [° C.] | Support | Dips [number] | Residence time in coating solution [s] | Coating content [%] |
| Comparative Example | 50 | PE rod | 3 | 3 | 45 |
| | 67 | free suspended | 3 | 30 | 56 |
| Example 3 | 35 | PE rod | 3 | 3 | 47 |
| | 50 | free suspended | 3 | 3 | 57 |

TABLE 4-continued

| | Coating parameters | | | | |
|---|---|---|---|---|---|
| Polymer | Temperature [° C.] | Support | Dips [number] | Residence time in coating solution [s] | Coating content [%] |
| Example 4 | 75 | PE rod | 4 | 3 | 48 |
| Example 6 | 40 | PE rod | 3 | 3 | 49 |
| | 30 | PE rod | 3 | 3 | 50 |
| | 30 | PE rod | 4 | 3 | 57 |
| | 30 | free suspended | 3 | 3 | 55 |
| Example 7 | 30 | PE rod | 3 | 3 | 47 |
| | 30 | PE rod | 3 | 3 | 47 |
| | 30 | PE rod | 4 | 3 | 55 |
| | Gelling: 24 h at 5° C. Coating: 30° C. | free suspended | 4 | 3 | 61 |
| Example 8 | 1 × 50° C.; 5° C. | PE rod | 4 | 1 × 30, 3 × 3 | 56 |
| | Gelling: 0° C. Coating: 25° C. | PE rod | 4 | 3 | 52 |
| | Gelling: 24 h at 5° C. Coating: 25° C. | PE rod | 3 | 3 | 51 |
| | Gelling: 24 h at 5° C. Coating: 25° C. | PE rod | 4 | 3 | 58 |
| | Gelling: 24 h at 5° C. Coating: 25° C. | PE rod | 3 | 3 | 53 |
| | Gelling: 24 h at 5° C. Coating: 25° C. | PE rod | 4 | 3 | 59 |

A coating gradient on the prosthesis is prevented by continuously turning the pros-theses during drying. In addition, the dip cycles are carried out with prostheses turned inside out each time and/or rotated with respect to the dipping direction.

After drying, the prostheses are shirred to 12 cm and dried and fixed at 60° C. for 30 min. After packaging and an ethylene oxide (EO) sterilization of the prostheses through the gas-permeable and bacterially tight packaging (Tyvek® cover films), the packaged prostheses are finally dried at 50° C. for 24 hours with vacuum cycles and dry air ($H_2O$ content: <1 ppm) and finally sealed with a vapor barrier by means of an aluminum/paper/PE cover foil.

TABLE 5

| | Data of accelerated polymer degradation study (in vitro) | | | |
|---|---|---|---|---|
| | Coating remaining after [%] | | | |
| Polymer | 22 days | 33 days | 42 days | 54 days |
| Comparative Example | 97 | 95 | 94 | 92 |
| Example 3 | 94 | 91 | 85 | 75 |
| Example 4 | 95 | 91 | 88 | 83 |
| Example 6 | 94 | 87 | 81 | 59 |
| Example 7 | 92 | 85 | 78 | 55 |
| Example 8 | 93 | 84 | 67 | 29 |

Degradation Studies (In Vitro)

This study was carried out with test specimens (Ø: 0.5 in., thickness: 0.07 in.) in phosphate buffer (pH=12) at 37° C.

Degradation of the polymer according to the Comparative Example, at 56 days to 92% of the original polymer mass, was distinctly slower than that of the other polymers.

The polymers of Examples 1 to 8 were maximally degraded down to 29% within the first 54 days.

In Vivo Degradation Studies

The absorption times from the functional one year long term animal study in sheep of prostheses coated with the comparative polymer showed on explanted prostheses even after 12 months polymer residues which caused inflammatory tissue reactions.

The degradation studies carried out with coated prostheses in a rat small animal study confirmed the degradation results of the polymers from the accelerated in vitro test. After 4 weeks no coating residues are detectable of the polymer according to Example 8. In the case of Example 6, as with Example 7, only minimal residues of the coating are found. Detachment of the coating was not observed for the polymers according to Examples 1 to 8.

TABLE 6

| Rat subcutaneous in vivo polymer degradation after 4 weeks | | |
|---|---|---|
| Polymer | Residues semiquantitative | Standard deviation |
| Example 6 | 0.17 | 0.4 |
| Example 7 | 1 | 0 |
| Example 8 | 0 | 0 |
| Comparative Example | 2.2 | 0.4 |

We claim:

1. A textile vascular prosthesis having a coating comprising an absorbable polymer in the form of a three-armed polyester having terminal hydroxyl groups from hydroxy acids polymerized onto a central trifunctional hydroxy compound, the three arms being tetrapolymers of lactide, ε-caprolactone, trimethylene carbonate and glycolide, wherein the polymer is composed of about 30 to about 45 mol % of lactide, about 20 to about 40 mol % of ε-caprolactone, about 10 to about 28 mol % of trimethylene carbonate and about 10 to about 25 mol % of glycolide.

2. The vascular prosthesis as claimed in claim 1, wherein the polymer is a segmented polymer comprising three first segments connected by the trifunctional hydroxy compound and three second segments connected to free ends of the first segments, the first segments differing from the second segments.

3. The vascular prosthesis as claimed in claim 2, wherein the first segment is free of lactide.

4. The vascular prosthesis as claimed in claim 2, wherein the second segment is free of trimethyl carbonate.

5. The vascular prosthesis as claimed in claim 2, wherein the first segment consists of caprolactone, trimethylene carbonate and glycolide.

6. The vascular prosthesis as claimed in claim 2, wherein the second segment consists of lactide, glycolide and optionally caprolactone.

7. The vascular prosthesis as claimed in claim 2, wherein the second segment is free of caprolactone.

8. The vascular prosthesis as claimed in claim 2, wherein the first segment contains about 30 to about 40 mol % of caprolactone, based on the total amount of the monomers in the two segments.

9. The vascular prosthesis as claimed in claim 2, wherein the first segment contains about 10 to about 20 mol % of trimethylene carbonate, based on the total amount of the monomers in the two segments.

10. The vascular prosthesis as claimed in claim 2, wherein the first segment contains about 7 to about 12 mol % of glycolide, based on the total amount of the monomers in the two segments.

11. The vascular prosthesis as claimed in claim 2, wherein the second segment contains about 30 to about 45 mol % of lactide, based on the total amount of the monomers in the two segments.

12. The vascular prosthesis as claimed in claim 2, wherein the second segment contains about 0 to about 4 mol % of caprolactone, based on the total amount of the monomers in the two segments.

13. The vascular prosthesis as claimed in claim 2, wherein the second segment contains about 1 to about 10 mol % of glycolide, based on the total amount of the monomers in the two segments.

14. A vascular prosthesis, wherein the coating polymer is in the form of a mixture of at least two different polymers according to claim 1.

* * * * *